United States Patent [19]

Adams et al.

[11] Patent Number: 5,496,855
[45] Date of Patent: Mar. 5, 1996

[54] ANTI-INFLAMMATORY COMPOUNDS

[75] Inventors: Jerry L. Adams; Ravi S. Garigipati, both of Wayne; Margaret E. Sorenson, Swedesburg; James D. Winkler, Fort Washington, all of Pa.

[73] Assignee: SmithKline Beecham Corp., Philadelphia, Pa.

[21] Appl. No.: 380,464

[22] Filed: Jan. 27, 1995

[51] Int. Cl.$^6$ .................. A61K 31/275; C07C 255/44; C07C 255/33

[52] U.S. Cl. .................. 514/521; 514/523; 558/390; 558/392; 558/394

[58] Field of Search .................. 558/392, 390, 558/394; 514/521, 523

[56] References Cited

U.S. PATENT DOCUMENTS

| | | | |
|---|---|---|---|
| 4,788,205 | 11/1988 | Cooper et al. | 514/333 |
| 4,801,598 | 1/1989 | Cooper et al. | 514/333 |
| 4,873,259 | 10/1989 | Summers, Jr. et al. | 514/443 |
| 4,933,365 | 6/1990 | Marshall et al. | 514/475 |
| 4,959,357 | 9/1990 | Reers et al. | 514/103 |
| 4,981,860 | 1/1991 | Tsushima et al. | 514/307 |
| 4,983,592 | 1/1991 | Wissner et al. | 514/92 |
| 4,992,455 | 2/1991 | Enomoto et al. | 514/342 |
| 5,002,941 | 3/1991 | Adams et al. | 514/186 |
| 5,011,847 | 4/1991 | Bitfu et al. | 514/336 |
| 5,019,581 | 5/1991 | Khanna et al. | 514/303 |
| 5,208,223 | 5/1993 | Wissner et al. | 514/92 |
| 5,208,244 | 5/1993 | Weiss | 514/336 |

*Primary Examiner*—Joseph Paul Brust
*Attorney, Agent, or Firm*—Dara L. Dinner; Stephen Venetianer; Edward T. Lentz

[57] ABSTRACT

This invention relates to the novel compounds and pharmaceutical compositions of Formulas (I) and (II).

This invention also relates to a method of treating or reducing inflammation in a mammal in need thereof, which comprises administering to said mammal an effective amount of a compound or composition of Formula (I) or (II).

11 Claims, No Drawings

ANTI-INFLAMMATORY COMPOUNDS

FIELD OF THE INVENTION

This invention relates to pharmaceutical compositions and their use as antiinflammatory agents in mammals.

BACKGROUND OF THE INVENTION

An early event in the response of most inflammatory cells to immunologic activation and other stimuli is the release of newly formed products (mediators) which alter the function and biochemistry of surrounding cells and tissues. The ensuing biological responses, as well as much of the pathogenesis which is attributed to inflammation and allergy, are thought to be dependent on the effects that these newly-formed mediators have on adjacent cells within the inflammatory region.

In the last 20 years, it has become apparent that lipid mediators are among the most potent and important products which are generated during inflammatory reactions. The synthesis of most lipid mediators is initiated by the specific cleavage of complex phospholipid molecules which contain arachidonate at their sn-2 position. Arachidonic acid is predominantly found in the sn-2 position of phospholipids after redistribution by transacylases and its release by sn-2 acylhydrolases from phospholipids represents the rate-limiting step in the formation of eicosanoids (leukotrienes, prostaglandins and thromboxanes) and other hydroxylareal fatty acids. As arachidonic acid is released, it is then convened to oxygenareal derivatives by at least two enzymatic systems (lipoxygenase and/or cyclooxygenase). Concomitant with arachidonate release, lysophospholipids are formed. One of these lyso phospholipids, 1-alkyl-2-lyso-sn-glycero-3-phosphocholine, is then acetylated to form platelet-activating factor (PAF). Each of the cell types involved in the inflammatory response produce and secrete a unique subset of lipid mediators. The quantities and nature of the metabolites depend on which enzymes and precursor phospholipid pools are available to inflammatory cells.

Once lipid mediators such as PAF and eicosanoids are formed by the aforementioned pathways, they induce signs and symptoms observed in the pathogenesis of various inflammatory disorders. Indeed, the pathophysiological activity of arachidonic acid (and its metabolites) is well known to those skilled in the art. For example, these mediators have been implicated as having an important role in allergy, asthma, anaphylaxis, adult respiratory distress syndrome, reperfusion injury, inflammatory bowel disease, rheumatoid arthritis, endotoxic shock, and cardiovascular disease. Aalmon et al., Br. Meal. Bull (1978) 43:285–296; Piper et al., Ann. NY Acad. Sci. (1991) 629:112–119; Holtzman, Am. Rev. Respir. Dis. (1991) 143:188–203; Snyder, Am. J. Physiol. Cell Physiol. (1990) 259:C697–C708; Prescott et at., J. Biol. Chem. (1990) 265:17381–17384.

Similar to arachidonate products, PAF is a potent proinflammatory mediator produced by a variety of cells. In vitro, PAF stimulates the movement and aggregation of neutrophils and the release therefrom of tissue-damaging enzymes and oxygen radicals. PAF has also been implicated in activation of leukocytes, monocytes, and macrophages. These activities contribute to the actions of PAF as having (pathological) physiological activity in inflammatory and allergic responses. PAF has also been implicated in smooth muscle contraction, pain, edema, hypotensive action, increases in vascular permeability, cardiovascular disorders, asthma, lung edema, endotoxin shock, and adult respiratory distress syndrome. PAF elicits these responses either directly through its own cellular receptor(s) or indirectly by inducing the synthesis of other mediators.

Accordingly, a method which antagonises the production of free arachidonic acid, its metabolites or PAF will have clinical utility in the treatment of a variety of allergic, inflammatory and hypersecretory conditions such as asthma, arthritis, rhinitis, bronchitis and urticaria, as well as reperfusion injury arid other disease involving lipid mediators of inflammation. Many published patent applications or issued U.S. patents exist which describe various compounds having utility as PAF or eicosanoid antagonists. Such patents include U.S. Pat. Nos. 4,788,205, 4,801,598, 4,981,860, 4,992,455, 4,983,592, 5,011,847, 5,019,581 and 5,002,941.

Phospholipase $A_2$'s ($PLA_2$(EC 3.1.1.4)) are responsible for the liberation of arachidonic acid from the sn-2 position of phospholipid. They are thought to play an important role in the pathogenesis of inflammation and possibly in immunological dysfunction, both as a cell associated enzyme as well as an extracellular soluble enzyme. Low molecular weight, mammalian Type II 14 kDa $PLA_2$ has been well characterized and is known to exist in both an extracellular form in inflammatory fluids (Kramer et at., J. Biol. Chem., 264:5768–5775 (1989) and in a cell associated form (Kanda et al., Biochemical and Biophysical Research Communications, 163:42–48 (1989) and has been found in a variety of cells and tissues or extracellularly when released in response to antigenic activators or pro-inflammatory mediators such as Interleukin (IL)-1, IL-6 or tumor necrosis factor (TNF). Its presence in such inflammatory fluids, tissue exudates or serum has therefore implicated Type II-14 kDa-$PLA_2$'s role in inflammation (Vadas, et at., (1985) Life Sci. 36, 579–587; and Seilhamer, et at., (1989) J. Biol. Chem. 264, 5335–5338). Recently, the elevated serum levels of $PLA_2$ activity during an inflammatory insult have been attributed to cytokine induction of acute phase protein release from liver, of which the 14 kDa-$PLA_2$ is suggested to be a part (Crowl, et al., (1991) J. Biol. Chem. 266, 2647–2651 ). In addition, soluble $PLA_2$ activity is markedly elevated in the serum and synovial fluid of patients with rheumatoid arthritis (Stefahski et al., J. Biochem. 100:1297–303 (1986). Furthermore, increasing serum $PLA_2$ levels have been shown to positively correlate with clinical severity (Bomalaski and Clark, Arthritis and Rheumat. 36:190–198 (1993)).

Various inhibitors of $PLA_2$ have been described in publications and in U.S. Patents. See for instance U.S. Pat. Nos. 4,959,357; 4,933,365; 5,208,223; 5,208,244; Marshall et at., J. Rheumatology 18:1 (1991); Marshall et at., Phospholipase $A_2$, Ed. Pyu Wong, Plenum Press, N.Y. (1990) pages 169–181; Wilkerson, et at., Eur. J. Med. Chem., 26:667, 1991; Wilkerson, Antiinflammatory Phospholipase $A_2$ Inhibitors, Drugs of the Future, Vol. 15, No. 2 p 139–148(1990) and Bennion et al., WO 91/08737 published 27 Jun. 1991.

Bennion et at., supra, discloses compounds having the general formula $R_1$-CON($R_5$)— C($R_2$)H—$(CH_2)n$—[Y$(CH_2)$p]q—COR_3 wherein interalia, $R_1$ is an alkyl group optionally substituted by an aryl, or hydroxy or cycloalkyl; $R_5$ is H, aryl, alkyl or alkenyl; Y is $CHR_6$, —CH=CH, O or S; and $R_3$ is OH, alkoxy, or $NHR_{31}$ and $R_{31}$ is hydrogen, alkyl, OH, or alkoxy optionally substituted by an aryl group.

Accordingly, as $PLA_2$ is important in the liberation of arachidoninc acid from phospholipid and may also play a role in the generation of PAF via lysophospholipid formation, inhibition of such an enzyme would be useful for the treatment of disease states caused thereby.

There are many novel forms of phospholipase A2's which have recently been discovered. For the purposes herein, members of the sn-2 acylhydrolase family of PLA2's are divided into low and high molecular weight enzymes be it from mammalian, or non-mammalian sources. Low molecular weight PLA$_2$'s will generally have a molecular weight in the range of 12,000 to 15,000. High molecular weight will be in the range of 30,000 or 56,000 kDa to 110,000 by SDS electrophoresis analysis.

A high molecular weight, cytosolic 85 kDa PLA$_2$ has been isolated and cloned from the human moncytic cell line, U937 (Clark et al., Proc. Natl. Acad. Sci., 87:7708–7712, 1990). The cell-associated Type II-14 kDa-PLA$_2$ in cell lipid metabolism was thought to be the key rate limiting enzyme in lipid mediator formation, until the recent identification of this cell-associated but structurally distinct 85 kDa sn-2 acylhydrolase, (Clark, et al., supra); and Kramer, et at., (1991) J. Biol. Chem. 266, 5268–5272. Like the Type II-14 kDa enzyme, this enzyme is active at neutral pH and Ca$^{2+}$-dependent, but in contrast exhibits a preference for AA in the sn-2 position of phospholipid substrate and migrates from the cytosol to the membrane in a Ca$^{2+}$-dependent manner and is regulated by phosphorylation (Kramer et al., J. Biol. Chem., 266:5268–5272 (1991). The 85 kDa-PLA$_2$ is also distinct from 14 kDa-PLA$_2$s and Ca$^{2+}$-independent PLA$_2$ as demonstrated by different biochemical characteristics such as stability of the 85 kDa-PLA$_2$ to DTT, instability to heat and the lack of inhibition by a phosphonate phospholipid TSA inhibitor of 14 kDa-PLA$_2$. In addition, 85 kDa-PLA$_2$ has been shown to possess a lysophospholipase A$_1$ activity which is not observed with the 14 kDa-PLA$_2$s. The 85 kDa enzyme is similar to the myocardial Ca$^{2+}$-independent PLA2 (Bomalaski and Clark, Arthritis and Rheumat. 36:190–198. (1993)) in that Ca$^{2+}$ is not required for catalysis and DTNB inhibition is observed. However, 85 kDa-PLA$_2$ is not inhibited by the suicide inactivator bromoenol lactone, suggesting that the enzyme is distinct from the myocardial enzyme as well.

These characteristics make the 85 kDa-PLA$_2$ a candidate for participation in the liberation of AA from phospholipid stores for subsequent metabolism to lipid mediators. Both the cytosolic 85 kDa PLA$_2$ and a cell associated Type II 14 kDa PLA$_2$ have been found in the human monocyte, neutrophil and platelet (Marshall and Roshak, Biochem. Cell Biol. 71:331–339 (1993)). As noted above, most of the cellular lipid mediators found elevated in a variety of inflammatory fluids are formed in response to non-pancreatic 14 kDa PLA$_2$ action. Since arachidonate-containing phospholipids are the key precursors for a broad range of lipid mediators it would not be surprising that inflammatory cells would treat these phospholipids differently than other fatty acid-containing phospholipids. In particular, there are enzymes which control the amount of arachidonate in different phospholipid pools and these enzymes are tightly regulated to maintain arachidonate homeostasis. The movement of arachidonate into and from all phospholipids was originally thought to be exclusively by Coenzyme A-dependent acyl transferase activitites. Holub et at., Adv. Lipid Res., 16:1–125 (1978); Lands et at., In The Enzymes of Biological Membranes, ed. Martonosi, A., pp. 3–85, Plenum Press, N.Y., 1976. However, it has now been demonstrated that an enzyme, Coenzyme A-independent transcylase (CoA-IT), is involved in the movement of 20 carbon higher unsaturated fatty acids, particularly arachidonate, into particular (1-alkyl- and 1-alkenyl) phospholipid pools. These are the phospholipid pools of arachidonate that are preferentially mobilized during cell activation and utilized for eicosanoid and PAF biosynsthesis, respectively.

CoA-IT has a specificity for certain phospholipids as donor and acceptor molecules. The fatty acid transferred is long chained and unsaturated, and almost exclusively arachidonate. Other fatty acids such as the 16:0, 18:1 or 18:2 are not moved into the sn-2 position of alkyl and 1-alkenyl phospholipid pools by CoA-IT. The specificity of CoA-IT is in direct contrast to many other CoA-dependent acylation activities which acylate a wide variety of lysophospholipids with no selectivity for arachidonate.

Accordingly, as CoA-IT is involved in arachidonic acid and phospholipid metabolism, inhibition of such an enzyme would be useful for the treatment of inflammatory, allergic and hypersecretory conditions or disease states caused thereby. Therefore, a method by which CoA-IT is inhibited will consequently and preferentially decrease the arachidonate content of 1-alkyl- and 1-alkenyl-linked phospholipids and will therefore decrease the production of pro-inflammatory mediators such as free arachidonic acid, prostaglandins, leukotriene and PAF during an inflammatory response.

SUMMARY OF THE INVENTION

This invention relates to the novel pharmaceutical compositions of Formula (I) and Formula (II) comprising a compound of Formula (I) and/or (II), or pharmaceutically acceptable salt thereof and a pharmaceutically acceptable diluent or carrier.

This invention also relates to a method of treating or reducing inflammation in a mammal in need thereof, which comprises administering to said mammal an effective amount of a compound or composition of Formula (I) or (II).

This invention also relates to a method of treating disease or disorders mediated by free arachidonic acid, its metabolites and/or PAF by administering to a patient in need thereof, an effective amount of a compound of Formula (I) or (II).

This invention also relates to a method of treating disease or disorders mediated by phospholipase A$_2$ by administering to a patient in need thereof, an effective amount of a compound or composition of Formula (I).

This invention also relates to a method of treating disease or disorders mediated by Coenzyme A independent transacylase by administering to a patient in need thereof, an effective amount of a compound or composition of Formula (II).

Another aspect of the present invention are the compounds represented by the structure having the formula:

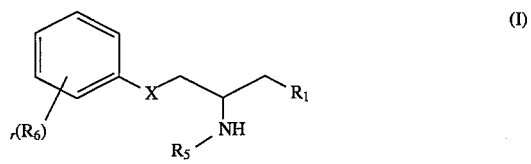

(I)

wherein

R$_1$ is cyano, —(CR$_{10}$R$_{11}$)—N—(OR$_2$)—C(Z)—R$_4$ or —(CR$_{10}$R$_{11}$)—N—(OR$_2$)R$_8$;

R$_2$ is hydrogen, a pharmaceutically acceptable cation, aroyl or a C$_{1-12}$ alkanoyl;

R$_4$ is NR$_8$R$_9$, alkyl$_{1-6}$; halosubstituted alkyl$_{1-6}$; hydroxy substituted alkyl$_{1-6}$; alkenyl$_{2-6}$; aryl or heteroaryl optionally substituted by halogen, alkyl$_{1-6}$, halosubstituted alkyl$_{1-6}$, hydroxyl, or alkoxy$_{1-6}$;

R$_5$ is C(O)(CH$_2$)$_q$aryl or S(O)$_2$(CH$_2$)$_q$aryl;

q is an integer having a value of 1 to 18;

X is carbon, oxygen, —$NC_{1-4}$ alkyl, or sulfur;

Z is oxygen or sulfur;

$R_{10}$ and $R_{11}$ are independently hydrogen or $C_{1-4}$ alkyl;

$R_8$ is independently hydrogen or $alkyl_{1-6}$; $R_9$ is hydrogen, $alkyl_{1-6}$, aryl, benzyl, heteroaryl, alkyl substituted by halogen or hydroxyl, or phenyl substituted by a member selected from the group consisting of halo, cyano, $alkyl_{1-12}$, $alkoxy_{1-6}$, halosubstituted $alkyl_{1-6}$, alkylthio, alkylsulphonyl, or alkylsulfinyl; or $R_8$ and $R_9$ may together with the nitrogen to which they are attached form a ring having 5 to 7 members, which members may be optionally replaced by a heteroatom selected from oxygen, sulfur or nitrogen;

$R_6$ is independently selected from hydrogen, halogen, $alkyl_{1-5}$, $cycloalkyl_{5-8}$, hydroxy, $(CHY)_t$carboxy, $alkoxy_{1-5}$, $thioalkyl_{1-5}$, $sulphinylalkyl_{1-5}$, $sulphonylalkyl_{1-5}$, halosubstituted $alkyl_{1-6}$, $(CHY)_tN(R_8)_2$, cyano or an optionally substituted aryl $C_{1-4}$ alkyl;

r is an integer having a value of 1 to 3;

t is a number having a value of 0 or 1;

Y is hydrogen or $alkyl_{1-4}$;

or pharmaceutically acceptable salt thereof.

Another aspect of the present invention are the compounds represented by the structure having the formula:

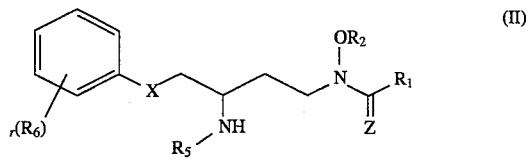

(II)

wherein $R_1$ is $NR_8R_9$, $alkyl_{1-6}$; halosubstituted $alkyl_{1-6}$; hydroxy substituted $alkyl_{1-6}$; $alkenyl_{2-6}$; aryl or heteroaryl optionally substituted by halogen, $alkyl_{1-6}$, halosubstituted $alkyl_{1-6}$, hydroxyl, or $alkoxy_{1-6}$;

$R_2$ is hydrogen, a pharmaceutically acceptable cation, aroyl or a $C_{1-12}$ alkanoyl;

$R_5$ is $C(O)(CH_2)_q$aryl or $S(O)_2(CH_2)_q$aryl;

q is an integer having a value of 1 to 18;

X is carbon, oxygen, $NC_{1-4}$alkyl, or sulfur;

Z is oxygen or sulfur;

$R_8$ is independently hydrogen or $alkyl_{1-6}$;

$R_9$ is hydrogen, $alkyl_{1-6}$, aryl, benzyl, heteroaryl, alkyl substituted by halogen or hydroxyl, or phenyl substituted by a member selected from the group consisting of halo, cyano, $alkyl_{1-12}$, $alkoxy_{1-6}$, halosubstituted $alkyl_{1-6}$, alkylthio, alkylsulphonyl, or alkylsulfinyl; or $R_8$ and $R_9$ may together with the nitrogen to which they are attached form a ring having 5 to 7 members, which members may be optionally replaced by a heteroatom selected from oxygen, sulfur or nitrogen;

$R_6$ is independently selected from hydrogen, halogen, $alkyl_{1-5}$, $cycloalkyl_{5-8}$, hydroxy, $(CHY)_t$carboxy, $alkoxy_{1-5}$, $thioalkyl_{1-5}$, $sulphinylalkyl_{1-5}$, $sulphonylalkyl_{1-5}$, halosubstituted $alkyl_{1-6}$, $(CHY)_tN(R_8)_2$, cyano or an optionally substituted aryl$C_{1-4}$alkyl;

r is an integer having a value of 1 to 3;

t is a number having a value of 0 or 1;

Y is hydrogen or $alkyl_{1-4}$;

or pharmaceutically acceptable salt thereof.

DETAILED DESCRIPTION OF THE INVENTION

The present invention is directed to a novel method of treating inflammatory disease in a mammal in need thereof by administering to said mammal an effective amount of a compound according to Formula (II) or (II). The compounds of Formula (I) and (II) may selectively inhibit the $PLA_2$ enzyme, the CoA-IT enzyme or both. Inhibition of either or both enzymes will result in the treatment of inflammatory occurrences in mammals. Inflammatory states in mammals may include, but are not limited to, allergic and asthmatic manifestations, dermatological diseases, inflammatory diseases, collagen diseases, reperfusion injury and stroke. Treatment of both acute and chronic diseases are possible. Preferred diseases for treatment are arthritis, asthma, allergic rhinitis, inflammatory bowel disease (IBD), psoriasis, reperfusion injury and stroke. For the purposes herein, the compounds of Formula (I) and (II) are preferential and selective inhibitors of the low molecular weight $PLA_2$ enzyme. The compounds of Formula (I) have been shown to selectively inhibit the $PLA_2$ enzyme and not inhibit in the invitro assay described herein the CoA-IT enzyme when $R_1$ is a nitrile functionality.

For compounds of Formula (I), $R_1$ is suitably cyano, —$(CR_{10}R_{11})$—N—$(OR_2)$—$C(Z)$—$R_4$ or —$(CR_9R_{10})$—N—$(OR_2)R_8$. Preferably $R_1$ is cyano or —$(CR_{10}R_{11})$—N—$(OR_2)$—$C(Z)$—$R_4$.

For compounds of Formula (I), $R_2$ is suitably hydrogen, a pharmaceutically acceptable cation, aroyl or a $C_{1-12}$ alkanoyl.

For compounds of Formula (I), $R_4$ is suitably $NR_8R_9$, $alkyl_{1-6}$; halosubstituted $alkyl_{1-6}$; hydroxy substituted $alkyl_{1-6}$; $alkenyl_{2-6}$; aryl or heteroaryl optionally substituted by halogen, $alkyl_{1-6}$, halosubstituted $alkyl_{1-6}$, hydroxyl, or $alkoxy_{1-6}$. Preferably $R_4$ is $NR_8R_9$.

For compounds of Formula (I), $R_5$ is suitably a $C(O)(CH_2)_q$aryl or $S(O)_2(CH_2)_q$aryl moiety; q is an integer having a value of 1 to 18. $R_5$ is preferably $C(O)(CH_2)_q$aryl; and q is preferably 5 to 10, more preferably 6. The aryl moiety may be optionally substituted independently one to three times by $(R_3)_v$; and v is an integer having a value of 1 to 3. The aryl is suitably phenyl or naphthyl, preferably phenyl.

$R_3$ is hydrogen, halogen, $alkyl_{1-5}$, $cycloalkyl_{5-8}$, hydroxy, $(CHY)_t$carboxy, $alkoxyl_5$, $thioalkyl_{1-5}$, $sulphinylalkyl_{1-5}$, $sulphonylalkyl_{1-5}$, halosubstituted $alkyl_{1-6}$, $(CHY)_tN(R_8)_2$ or cyano; t is 0 or an integer having a value of 1; and Y is hydrogen or $alkyl_{1-4}$; and $R_8$ is as defined below. Preferably $R_3$ is hydrogen.

For compounds of Formula (I), $R_8$ is suitably hydrogen or $alkyl_{1-6}$; and $R_9$ is suitably hydrogen, $alkyl_{1-6}$, aryl, benzyl, heteroaryl, alkyl substituted by halogen or hydroxyl, or phenyl substituted by a member selected from the group consisting of halo, cyano, $alkyl_{1-12}$, $alkoxy_{1-6}$, halosubstituted $alkyl_{1-6}$, alkylthio, alkylsulphonyl, or alkylsulfinyl; or $R_8$ and $R_9$ may together with the nitrogen to which they are attached form a ting having $_5$ to $_7$ members, which members may be optionally replaced by a heteroatom selected from oxygen, sulfur or nitrogen. Preferably $R_8$ and $R_9$ are both hydrogen.

For compounds of Formula (I), suitably $R_{10}$ and $R_{11}$ are independently hydrogen or $C_{1-4}$ alkyl.

For compounds of Formula (I), suitably $R_6$ is independently selected from hydrogen, halogen, $alkyl_{1-5}$, $cycloalkyl_{5-8}$, hydroxy, $(CHY)_t$carboxy, $alkoxy_{1-5}$, $thioalkyl_{1-5}$, $sulphinylalkyl_{1-5}$, $sulphonylalkyl_{1-5}$, halosubstituted $alkyl_{1-6}$, $(CHY)_tN(R_8)_2$, cyano or an optionally substituted aryl$C_{1-4}$ alkyl; and r is an integer having a value of 1 to 3; t is 0 or an integer having a value of 1; and Y is hydrogen or alkyl $_{1-4}$. Preferably $R_6$ is an optionally substituted aryl$C_{1-4}$ alkyl.

The aryl moiety of the arylalkyl group is optionally substituted independently by the moiety $(R_7)_s$; wherein s is an integer having a value of 1 to 3; and $R_7$ is selected from hydrogen, halogen, alkyl$_{1-5}$, cycloalkyl$_{5-8}$, hydroxy, $(CHY)_t$-carboxy, alkoxy$_{1-5}$, thioalkyl$_{1-5}$, sulphinylalkyl$_{1-5}$, sulphonylalkyl$_{1-5}$, halosubstituted alkyl$_{1-6}$, $(CHY)_tN(R_8)_2$, or cyano. The aryl alkyl group is preferably benzyl. $R_7$ is preferably hydrogen.

For compounds of Formula (I), Z is suitably oxygen or sulfur, preferably oxygen.

For compounds of Formula (I), X is suitably a carbon, a substituted nitrogen, oxygen or sulfur moiety, preferably oxygen.

Exemplified compounds of Formula (II) are: (±) N-[3-(7-phenylheptylamido)-4-(4-phenylmethyl)phenylthio]-butyl-N-hydroxy urea; or [(±)3-(7-Phenylheptylamido)-4-(4-phenylmethyl)phenylthio]butylnitrile.

For compounds of Formula (II), $R_1$ is suitably $NR_8R_9$, alkyl$_{1-6}$; halosubstituted alkyl$_{1-6}$; hydroxy substituted alkyl$_{1-6}$; alkenyl$_{2-6}$; aryl or heteroaryl optionally substituted by halogen, alkyl$_{1-6}$, halosubstituted alkyl$_{1-6}$, hydroxyl, or alkoxy$_{1-6}$.

For compounds of Formula (II), $R_2$ is suitably hydrogen, a pharmaceutically acceptable cation, aroyl or a $C_{1-12}$ alkanoyl.

For compounds of Formula (II), $R_5$ is suitably a $C(O)(CH_2)_q$aryl or $S(O)_2(CH_2)_q$aryl moiety; q is an integer having a value of 1 to 18. $R_5$ is preferably $C(O)(CH_2)_q$aryl; and preferably q is 5 to 10, more preferably 6. The aryl moiety may be optionally substituted independently one to three times by $(R_3)_v$; and v is an integer having a value of 1 to 3. The aryl is suitably phenyl or naphthyl, preferably phenyl.

$R_3$ is hydrogen, halogen, alkyl$_{1-5}$, cycloalkyl$_{5-8}$, hydroxy, $(CHY)_t$carboxy, alkoxy$_{1-5}$, thioalkyl$_{1-5}$, sulphinylalkyl$_{1-5}$, sulphonylalkyl$_{1-5}$, halosubstituted alkyl$_{1-6}$, $(CHY)_tN(R_8)_2$ or cyano; t is 0 or an integer having a value of 1; and Y is hydrogen or alkyl$_{1-4}$; and $R_8$ is as defined below. Preferably $R_3$ is hydrogen.

For compounds of Formula (II), suitably $R_6$ is independently selected from hydrogen, halogen, alkyl$_{1-5}$, cycloalkyl$_{5-8}$, hydroxy, $(CHY)_t$carboxy, alkoxy$_{1-5}$, thioalkyl$_{1-5}$, sulphinylalkyl$_{1-5}$, sulphonylalkyl$_{1-5}$, halosubstituted alkyl$_{1-6}$, $(CHY)_tNCR_8)_2$, cyano or an optionally substituted arylC$_{1-4}$ alkyl; and r is an integer having a value of 1 to 3; t is 0 or an integer having a value of 1; and Y is hydrogen or alkyl$_{1-4}$. Preferably $R_6$ is an optionally substituted arylC$_{1-4}$ alkyl.

The aryl moiety of the arylalkyl group is optionally substituted independently by the moiety $(R_7)_s$; wherein s is an integer having a value of 1 to 3; and $R_7$ is selected from hydrogen, halogen, alkyl$_{1-5}$, cycloalkyl$_{5-8}$, hydroxy, $(CHY)_t$-carboxy, alkoxy$_{1-5}$, thioalkyl$_{1-5}$, sulphinylalkyl$_{1-5}$, sulphonylalkyl$_{1-5}$, halosubstituted alkyl$_{1-6}$, $(CHY)_tN(R_8)_2$, or cyano. The aryl $C_{1-4}$ alkyl group is preferably benzyl. $R_7$ is preferably hydrogen.

For compounds of Formula (II), X is suitably a carbon, substituted nitrogen, oxygen or sulfur moiety, preferably oxygen.

For compounds of Formula (II), Z is suitably oxygen or sulfur, preferably oxygen.

Exemplified compounds of Formula (II) are:
(±) N-[$_3$-(7-phenylheptylamido)-4-(4-phenylmethyl)phenylthio]-butyl-N-hydroxy urea.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of compounds of formula (I) may also be formed with a pharmaceutically acceptable cation, for instance, if a substituent $R_1$ comprises a carboxy group. Suitable pharmaceutically acceptable cations are well known to those skilled in the art and include alkaline, alkaline earth, ammonium and quaternary ammonium cations.

The following terms, as used herein, refer to:

The terms "aryl" or "heteroaryl" are used herein at all occurrences to mean substituted and unsubstituted aromatic ring(s) or ring systems containing from 5 to 16 carbon atoms, which may include hi- or tri-cyclic systems and may include, but are not limited to heteroatoms selected from O, N, or S. Representative examples include, but are not limited to, phenyl, naphthyl, pyridyl, quinolinyl, thiazinyl, and furanyl.

The term "heterocyclic"—such as when R5 and R6 together with the nitrogen to which they are attached form a saturated 5–7 membered ring system in which the ring many contain one or more heteroatoms selected from the group consisting of N, O, or S; and may include, but is not limited to, pyrrolidine, piperidine, piperazine, or morpholine.

The terms "lower alkyl" or "alkyl" are used herein at all occurrences to mean straight or branched chain radical of 1 to 10 carbon atoms, unless the chain length is limited thereto, including, but not limited to methyl, ethyl, n-propyl, iso-propyl, n-butyl, sec-butyl, so-butyl, tert-butyl, and the like.

The term "alkenyl" is used herein at all occurrences to mean straight or branched chain radical of 2–10 carbon atoms, unless the chain length is limited thereto, including, but not limited to ethenyl, 1-propenyl, 2-propenyl, 2-methyl-1-propenyl, 1-butenyl, 2-butenyl and the like.

The term "aralkyl" is used herein to mean $C_{1-4}$ Ar, wherein Ar is as defined above; and the alkyl group may be branched or straight as also defined above, unless otherwise indicated.

The term "aroyl" is used herein to mean —C(O) Ar, wherein Ar is as defined above, including, but not limited to phenyl, 1- or 2-naphthyl and the like.

The term "alkanoyl" is used herein to mean —C(O)C$_{1-10}$, wherein alkyl is as defined above, including but not limited to methyl, ethyl, isopropyl, n-butyl, t-butyl, and the like.

The term "cycloalkyl" is used herein to mean cyclic radicals, preferably of 3 to 8 carbons, including but not limited to cyclopropyl, cyclopentyl, cyclohexyl, and the like.

The term "halo" or "halogen" are used interchangeably herein to mean radicals derived from the elements fluorine, chlorine, bromine, and iodine.

The compounds of the present invention may contain one or more asymmetric carbon atoms and may exist in racemic and optically active forms. All of these compounds are included within the scope of the present invention.

The present compounds of Formula (I) and (II) can be prepared by art-recognized procedures from known compounds. Several different synthetic schemes can be used to prepare the compounds of this invention and are described in greater detail below. In Scheme I below, compounds of Formula (I) are obtained wherein $R_1$ is cyano and X is generally O, S or N. While the schematic is representative of $R_3$, $R_6$, and $R_7$ as hydrogen it is merely illustrative and compounds wherein other R groups may obtained may also be prepared in an analogous manner.

Compounds of the formula I, can be prepared as illustrated in the scheme I. Commercially available 1 can be epoxidized under standard conditions with peracids such as MCPB A, trifluoroperacetic acid, peraceticacid, magnesium monoperphthalate in step a. The resulting epoxide 2 can be cleaved selectively with a variety of organic nucleophiles (ROH, RSH, $RNH_2$, where R is an alkyl or a substituted alkyl group) in step b to afford the alcohol 3. This alcohol 3 can be oxidized in step c, to the corresponding ketone 4, by a variety of common commercially available oxidants such as PCC, PDC, Dess-Martin Periodinane, etc. The oxidation can also be carried out by well known reactions like the Swern oxidation, or Collins Oxidation procedures. The ketone, in step d, can be converted to the amine 5 by reductive amination (e.g., in a one step reaction as shown with $NH_4OAc$ or $NH_4Br$ and $NaCNBH_4$ in MeOH or EtOH as solvents; or in a two step process which can involve conversion of the ketone 4 to an oxime, alkyloxime or an imine followed by a reduction with $NaBH_4$ or $NaCNBH_4$ or Raney Nickel, etc.). The amine 5 can be transformed into the compound of general formula I by acylation or suffonylation with the appropriate reagent $R_aX_a$ as shown in step e, wherein Ra is a suitable acyl or sulfonyl moiety and Xa is a suitable halide, such as with an acid halide, an acid anhydride, a sulfonyl halide, or a sulfonyl anhydride in a aprotic solvent.

In Scheme 2 below, compounds of Formula (I) and (II) are obtained wherein $R_1$ is other than cyano. The hydroxyurea moiety is obtained through the hydroxylamine intermediate. The various $R_4$ moieties may also be prepared in an analogous manner to those described in U.S. Patent Summers et at., U.S. Pat. No. 4,873,259, issued Oct. 10, 1989, pages 7–11, and Adams et at., WO 91/14674, published $_3$ Oct. 1991 whose disclosures are incorporated by reference herein in their entirety. Protection of the alcohol moiety of 3-buten-1-ol (e.g., t-butyldimethylsilyl group), followed by epoxidation with peracids such as MCPBA, trifluoroperacetic acid, peraceticacid, magnesium monoperphthalate leads to the compound 6. It is also recognized that other well known suitable silyl protecting groups may be used herein. Base catalyzed epoxide opening with thiol 7 yields the sulfide 8. Swern oxidation under any of the known conditions leads to ketone 9. Reductive amination and acylation as described above affords the amide 10.

SCHEME 1

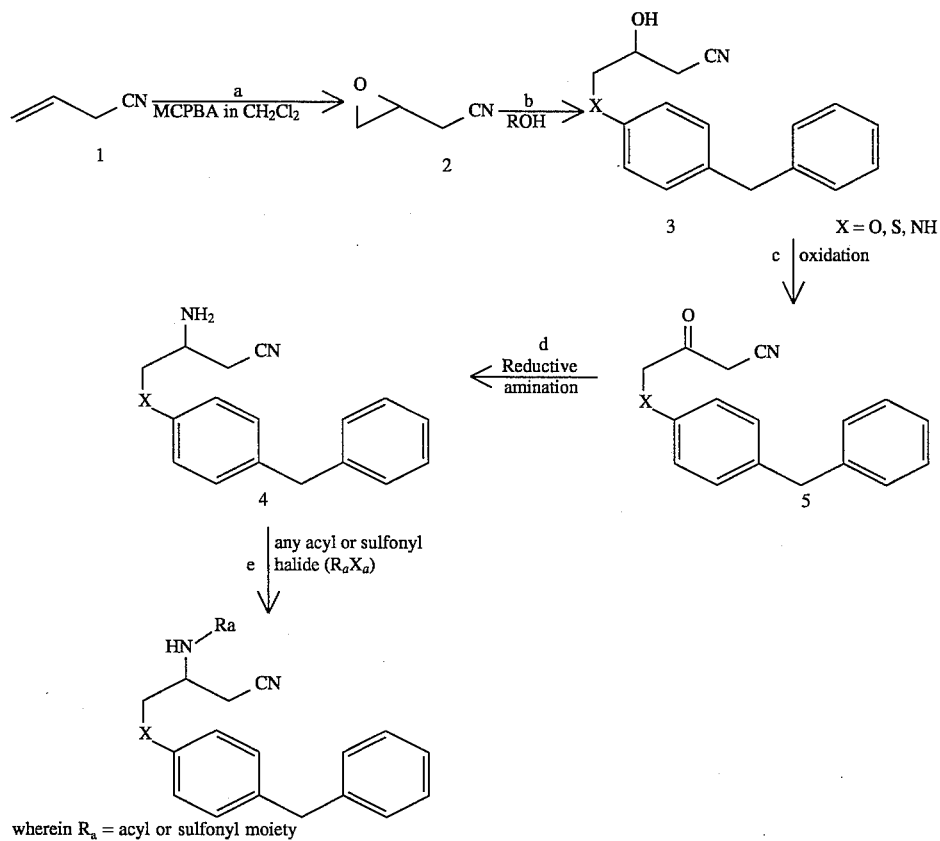

SCHEME 2

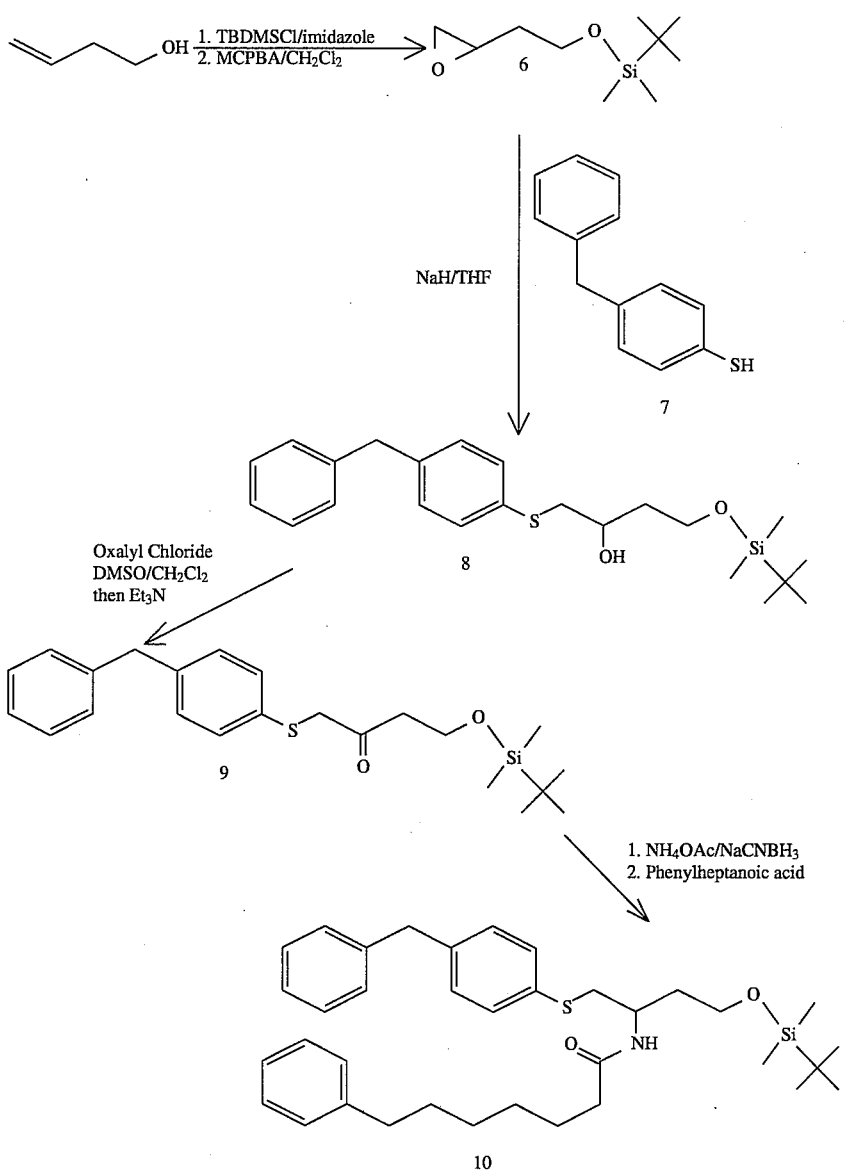

Deprotection of the silyl group of compound 10 can be accomplished under any of the standard conditions (TBAF/THF, TFA, HOAc etc.) well known in the art. This resulting alcohol can then be subjected to the Mitsunobu reaction with compound 11, to afford the key intermediate 12. Compound 12 can be converted to hydroxyurea 13, by treatment with methanolic ammonia. Compound 12 can also be converted to the hydroxylamine 14 by basic hydrolysis, which in turn can be transformed to a hydroxamic acid 15 (wherein R=alkyl or substituted alkyl).

SCHEME 3

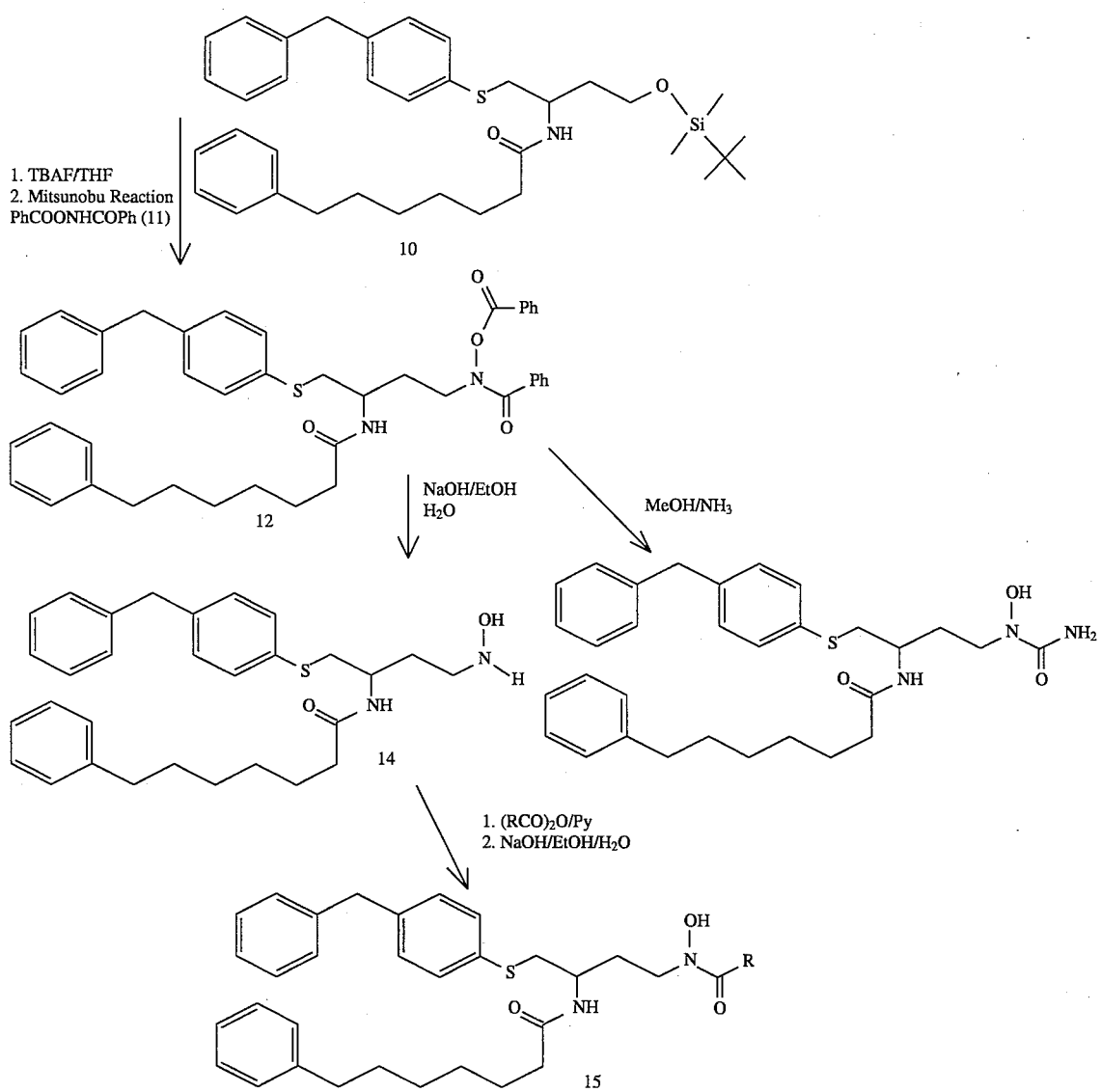

Suitable protecting groups for use with hydroxyl groups are well known in the art and described in many references, for instance, Protecting Groups in Organic Synthesis, Greene T W, Wiley-Interscience, New York, 1981. Suitable examples of hydroxyl protecting groups include silyl ethers, such as t-butyldimethyl or t-butyldiphenyl, and alkyl ethers, such as methyl connected by an alkyl chain of variable link, $(CR_{10}R_{20})_n$.

Pharmaceutically acid addition salts of compounds of Formula (I)/(II) may be obtained in known manner, for example by treatment thereof with an appropriate amount of acid in the presence of a suitable solvent.

Without further elaboration, it is believed that one skilled in the art can, using procedures analagous to those described herein, utilize the present invention to its fullest extent. The invention will now be described by reference to the following examples which are merely illustrative and are not to be construed as a limitation of the scope of the present invention.

SYNTHETIC CHEMISTRY

Temperatures are recorded in degrees centigrade unless otherwise noted.

Example 1

Preparation of N-[3-(7-phenylheptylamido)-4-(4phenylmethyl)phenylthio]-butyl-N--hydroxy urea a) 4-butene oxide-1-(tert-butyldiphenylsilyl)ol.

To a stirred mixture of meta-chloroperoxybenzoic acid (9.4 g, 34.8 mmol) in methylene chloride (350 ml) at 0° C. was added dropwise a solution of 4-butene-1-(tertbutyldiphenylsilyl)ol (9.02 g, 29.0 mmol) in methylene chloride (100 ml). After stirring at RT for 2 days, the reaction was quenched by the addition of saturated aqueous sodium bisulfite (2 ml) and saturated aqueous sodium bicarbonate (150 ml). After stirring for 30 min the organic phase was separated, washed with saturated sodium bicarbonate and water, and dried ($Na_2SO_4$). The solvent was evaporated and the resulting oil was purified by flash chromatography (silica gel, 7% ethylacetate/hexane) to yield the title compound (9.27 g, 98%). $^1$H NMR (400 MHz, CDCl$_3$) d 7.73 (m, 4H), 7.42 (m, 6H), 3.90 (m, 2H), 3.18 (M, 1H), 2.81 (t, 1H), 2.55 (t, 1H), 1.82(m, 2H), 1.15(s, 9H).

b) 4-(4-phenylmethyl)phenylthio-3-hydroxy-1-(tert-butyldiphenylsilyl)-butanol

To a solution of 4-mercapto-diphenyl methane (1.09 g, 5.45 mmol) and tetrahydrofuran (20 ml) was added sodium hydride (0.28 g, 60% suspension in mineral oil, 7.09 mmol). After stirring the resulting mixture 30 min, the compound from Example 1(a) (1.8 g, 5.45 mmol) was added. After stirring 1.5 h, the reaction was diluted with water and the product was extracted (ethyl acetate). The organic phase was dried (Na$_2$SO$_4$) and concentrated. The residue was purified by flash chromatography (silica gel, $_5$% ethyl acetate/hexane) to yield the title compound (2.48 g, 86%). 1H NMR (400 MHz, CDCl$_3$) d 7.70 (m, 4H), 7.45 (m, 6H), 7.34 (m, 4H), 7.23 (m, 3H), 7.13 (d, 2H), 4.0 3.99 (s, 2H), 3.89 (m, 2H), 3.05 (m, 2H), 1.84 (m, 2H), 1,09 (s, 9H).

c) 4-(4-phenylmethyl)phenylthio-3-oxo-butan-1-(tert-butyldiphenylsilyl)ol

A solution of oxalylchloride (0.46 ml, 5.02 mmol) and methylene chloride (12 ml) was cooled to −78° C. To this was added dropwise a solution of dimethylsulfoxide (0.78 ml, 11.01 mmol) in methylene chloride (2.5 ml) and the solution was stirred 5 min followed by the dropwise addition of the compound from Example 1(b) (2.40 g, 4.56 mmol) dissolved in methylene chloride (5 ml). After stirring at 78° C. for 2 h triethylamine (2.9 ml, 20.52 mmol) was added and the reaction was stirred an additional 5 min before warming to RT and diluting with water. The aqueous phase was extracted with methylene chloride and the organic phases were combined, washed with brine, dried (Na$_2$SO$_4$) and concentrated. The residue was purified by flash chromatography (silica gel, methylene chloride) to yield the title compound (2.03 g, 85%). 1H NMR (400 MHz, CDCl$_3$) d 7.70 (d, 4H), 7.50–7.06 (m, 15H), 3.95 (m, 4H), 3.72 (s, 2H), 2.85 (t, 2H), 1.06 d) 4-(4-phenylmethyl)phenylthio-3-amino-butan-1-(tert-butyldiphenylsilyl)ol

To a solution of the compound from Example 1(c) (1.52 g, 2.9 mmol) in methanol (20 ml) with 3 angstrom molecular sieves was added anhydrous ammonium acetate (2.2 g, 29.2 mmol) followed by sodium cyanoborohydride (0.15 g, 2.05 mmol). After stirring for 48 h the reaction mixture was filtered and the precipitate was rinsed with ethyl acetate. After evaporation of the solvents, the residue was diluted with water, made basic by the addition of solid KOH, and extracted with ethyl acetate. The solve to was evaporated and the residue was purified by flash chromatography (silica gel, 5%–10% ethyl acetate/hexane) to yield the title compound (0.49 g, 32%). $^1$H NMR (400 MHz, CDCl$_3$) d 7.65 (m, 4H), 7.50–7.05 (m, 15 H), 3.94 (s, 2H), 3.78 (t, 2H), 3.16 (m 1H), 3.09 (d, 1H), 1.78 (m 1H), 1.60 (m, 1H), 1.05 (s, 9H).

e) N-[$_3$-($_7$-phenylheptylamido)]-4-(4-phenylmethane)phenylthio-butan-1-(tert-butyldiphenylsilyl)ol To a solution of the compound from Example 1(d) (0.4874 g, 0.93 mmol) in methylene chloride (10 ml) were added 7-phenylheptanoic acid (0.2 mg, 1.02 mmol), 1-(3-dimethylaminopropyl)- 3-ethyl dimethylaminopropyl)-3-ethyl carbodiimide hydrochloride (0.20 gm 1.02 mmol) and a catalytic amount of 4-dimethyl amino pyridine. After stirring 18 h the mixture was poured directly onto a chromatography column and purification by flash chromatography (silica gel, methylene chloride) yielded the title compound (0.53 g, 80%). $^1$H NMR (400 MHz, CDCl$_3$) d 7.65 (m, 4H), 7.42 (m, 6H), 7.30 (m, 6H), 7.18 (m, 6H), 7.10 (d, 2H), 4.24 (m, $_1$H), 3.92 (s, 2H), 3.79 (m, 1H), 3.72 (m, 1H), 3.30 (dd, 1H), 3.00 (dd, 1H), 2.61 (q, 2H), 1.95 (t, $_3$H), 1.60 (m, 3H), 1.53 (m, 2H), 1.31 (m, 4H), 1.08 (s, 9 H).

f) N-[3-(7-phenylheptylamido)]-4-(4-phenylmethylphenylthio)-butan-1-ol

To a solution of the compound from Example 1(e) (0.0543 g, 0.076 mmol) in dry tetrahydrofuran (1 ml) at 0° C. was added tert-butylammonium fluoride (0.15 ml, 0.15 mmol 1M solution in THF). After stirring for 5 min the mixture was warmed to RT and stirred 6 h. After diluting with water and extracting with ethyl acetate, the organic phase was washed with brine then concentrated. The residue was purified by flash chromatography (silica gel, 50%–100% ethyl acetatehexane) to yield the title compound as a white solid (0.0317 g, 88%). $^1$H NMR (400 MHz, CDCl$_3$) d 7.30 (m,6H), 7.12 (d, 2H), 5.85 (d, 1H), 4.34 (m, 1H), 3.97 (s, 2H), 3.65 (m, 1H), 3.54 (m, 1H), 3.08 (m, 2H), 2.61 (t, 2H), 2.12 (t, 2H), 1.86 (m, 1H), 1.60 (m, 5H), 1.33 (m, 4H).

g) N-[3-(7-phenylheptylamido)]-4-(4-phenylmethyl)phenylthio-butyl-[(N-phenylcarbonate)-(N-phenylester)]-amine The compound from Example 1(f) was dissolved in dry tetrahydrofuran (0.5 ml). Added to this were N-(phenylcarbonate)-N-(phenylester)-amine (0.02 g, 0.073 mmol) and triphenylphosphene. After stirring for 5 min diethylazodicarboxylate (0.012 ml, 0.080 mmol) in dry tetrahydrofuran (0.1 ml) was added dropwise. After stirring the reaction at RT for 1 h the mixture was concentrated. The product was purified by flash chromatography (silica gel, 25% acetone/hexane) to yield the title compound (0.0102 g, 22%). $^1$H NMR (400 MHz, CDCl$_3$) d 7.60–7.10 (m, 24H), 5.95 (m, 1H), 4.30 (m, 1H), 3.98 (s, 2H), 3.90 (m, 2H), 3.22 (dd, 1H), 3.10 (m, 1H), 2.60 (m, 2H), 2.8 (m, 1H), 2.08 (m, 2H), 1.75 (m, 1H), 1.60 (m, 3H), 1.30 (m, 5H).

h) N-[3-(7-phenylheptylamido(-4-(4-phenylmethyl)phenylthio]-butyl-N-hydroxyurea

To a solution of the compound from Example 1(g) (0.075 g, 0.10 mmol) dissolved in methanol (1 ml) was added dropwise condensed ammonia gas. The flask was sealed and the solution was refluxed at RT for 8 h. The flask was vented and after stirring for 18 h the solution was concentrated. The residue was purified by flash chromatography (silica gel, 2% methanol/methylene chloride) to yield the title compound as a colorless off (0.0117 g, 23%). MS (±ESMS) m/e 534 [M]$^+$.

EXAMPLE 2

Preparation of [3-(7-Phenylheptylamido)-4-(4-phenylmethyl)phenylthiolbutylnitrile a) N-[3-(7-phenylheptylamido)-4-(4-phenylmethyl)phenylthio]butyl-N-hydroxyamine A mixture of the compound from Example 1(g) (0.02 g, 0.028 mmol), methanol (2 ml) and concentrated aqueous potassium hydroxide solution (0.5 ml) was stirred at 60° C. After 4 h the mixture was filtered and concentrated. The residue was taken up in water and extracted with methylene chloride. The organic phase was dried (Na$_2$SO$_4$) and concentrated. Purification by flash chromatography (silica gel, 25%–100% ethyl acetate/hexane) yielded the title compound (0.0072 g, 52%). $^1$H NMR (400 MHz, CDCl$_3$) d 7.30 (m, 7H), 7.17 (m, 7H), 5.81 (d, 1H), 4.25 (m,1H), 3.95 (s, 2H), 3.80 (m, 1H), 3.39 (m, 1H), 3.10 (t, 2H), 2.60 (t, 2H), 2.08 (t, 2H), 1.90 (m, 2H), 1.82 (m, 2H), 1.61 (m, 2H), 1.55 (m, 2H), 1.31 (m, 4H).

b) N-[3-(7-phenylheptylamido)-4-(4-phenylmethyl)phenylthio]-butyl-N-(O-acetyl)acetohydroxamic acid The compound from Example 2(a) (0.0161 g, 0.03 mmol) was stirred at 60° C. for 1 h in acetic anhydride (1 ml). The mixture was then washed with water and the solvent was concentrated. The product was purified by flash chromatography (silica gel, 10% ethyl acetate/hexane) to yield the title compound. $^1$H NMR (400 MHz, CDCl$_3$) d 7.30 (m, 7H), 7.15 (m, 7H), 5.66 (d, 1H), 4.20 (m, 1H), 3.94 (s, 2H), 3.25–3.00 (m, 2H), 2.80 (dd, 2H), 2.58 (t, 2H), 2.11 (t, 2H), 1.60 (m, 7H), 1.31 (m, 6H), 1.25 (s, 3H).

c) [3-(7-Phenylheptylamido)-4-(4-phenylmethyl)phenylthio]butylnitrile.

A solution of the compound from Example 2(b) in isopropanol was stirred with excess aqueous lithium hydroxide (1M solution). After 2 h the mixture was diluted with methylene chloride. The organic phase was washed with water and brine and dried (Na$_2$SO$_4$). The residue was purified by flash chromatography eluting with 25%–50% EtOAc/hexane to give the title compound (0.0014 g). $^1$H NMR (400MHz, CDCl$_3$) d 7.30 (m, 7H), 7.19 (m, 7H), 5.78 (d, 1H), 4.20 (m, 1H), 3.95 (s, 2H), 3.20 (dd, 1H), 3.05 (dd, 1H), 2.80 (t, 2H), 2.60 (t, 2H), 2.12 (t, 2H), 1.62 (m, 4H), 1.34 (m, 4 H). $^{13}$C NMR (400 MHz, CDCl$_3$) d 173.47, 142.92, 141.21, 140.72, 131.43, 131.35, 130.30, 129.21, 128.88, 128.70, 128.56, 126.60, 125.94, 117.23, 46.15, 41.74, 37.61, 36.72, 36.16, 31.55, 29.33, 29.21, 25.66, 22.29.

METHODS OF TREATMENT

The compounds of Formula (I)/(II), or pharmaceutically acceptable salts thereof, can be used in the manufacture of a medicament for the prophylactic or therapeutic treatment of an inflammatory disease state in a mammal, preferably a human.

Inhibition of PLA$_2$ and/or CoA-IT and the simultaneous reduction of PAF, free arachidonic acid and eicosanoid release from inflammatory cells according to this invention is of therapeutic benefit in a broad range of diseases or disorders. The invention herein is therefore useful to treat such disease states both in humans and in other mammals.

Inhibition of CoA-IT and 14 kDa PLA$_2$ by the compounds of Formula (I) and/or Formula (II) is an effective means for simultaneously reducing PAF, free arachidonic acid and eicosanoids produced in inflammatory cells. The therapeutic utility of blocking lipid mediator generation has been recognized for many years. For example, inhibitors of cyclooxygenase, such as aspirin, indomethacin, acetaminophen and ibuprofen, have demonstrated broad therapeutic utilities. CoA-IT inhibitors inhibit cyclooxygenase products. Another class of inhibitors which are used in a broad range of inflammatory disorders are the corticosteroids. Corticosteroids act in a variety of ways, e.g. to induce inflammatory cells to produce proteins which inhibit free arachidonic acid release or to down regulate PLA$_2$ mRNA formation. Both 14 kDa PLA$_2$ inhibitors and CoA-IT inhibitors block the release of free arachidonic acid. Inhibitors of 5-lipoxygenase block the production of leukotrienes and leukotriene antagonists prevent the bioactions of leukotrienes. Recent studies indicate that both will have broad therapeutic utilities. Both 14 kDa PLA2 inhibitors and CoA-IT inhibitors block the production of leukotrienes. Inhibitors of phospholipase A$_2$ block the release of free arachidonic acid and the formation of lyso PAF (the immediate precursor of PAF). PLA$_2$ inhibitors are recognized to have broad therapeutic utilities. It does not, however, follow that the disease states noted above must in fact be caused by altered CoA-IT or PLA$_2$ activity. Thus, the disease state itself may not be directly mediated by CoA-IT or PLA$_2$ activity. It only follows that CoA-IT or PLA$_2$ activity is required for the continued expression of symptoms of the disease state and that CoA-IT or PLA$_2$ inhibitors will be beneficial against the symptoms of these disease states.

Recognition that 14 kDa PLA2 and/or CoA-IT inhibitors reduce PAF production has a number of therapeutic implications. PAF itself has been implicated as being involved in a number of medical conditions. Thus in circulatory shock, which is characterised by systemic hypotension, pulmonary hypertension and increased lung vascular permeability, the symptoms can be mimicked by infusion of PAF. This coupled with evidence showing that circulating PAF levels are increased by endotoxin infusion indicate that PAF is a prime mediator in certain forms of shock.

Intravenous infusion of PAF at doses of 20–200 pmol kg<–1>min<–1> into rats has been reported to result in the formation of extensive haemorrhagic erosions in the gastric mucosa. Thus PAF is the most potent gastric ulcerogen yet described whose endogenous release may underlie or contribute to certain forms of gastric ulceration. Psoriasis is an inflammatory and proliferative disease characterised by skin lesions. PAF is pro-inflammatory and has been isolated from lesioned scale of psoriatic patients indicating PAF has a role is the disease of psoriasis. And finally, increasing evidence supports a potential patho-physiological role for PAF in cardiovascular disease. Thus recent studies in angina patients show PAF is released during atrial pacing. Intracoronary injection of PAF in pigs induces a prolonged decrease in coronary flow and, in guines pig hearts, it induces regional shunting and ischaemia. In addition PAF has been shown to initiate thrombus formation in a mesenteric artery preparation, both when administered exogenously and when released endogenously. More recently PAF has been shown to play a role in brain ischaemia induced in animal models of stroke. Thus the compounds of the invention, by virtue of their ability to antagonise either CoA-IT and/or PLA$_2$, thus block the production of PAF, free arachidonic acid and its metabolites, are likely to be of value in the treatment of any of the above conditions.

The action of a PLA$_2$ inhibitor can be distinguished from the activity of a CoA-IT inhibitor based on their specific actions on their respective enzymes and by their different effects in cellular assays. For example only CoA-IT inhibitors have the ability to interfere with the mobilization of radiolabelled arachidonic acid to move from the alkyl-PC pool to the alkenyl PE pool. Selective inhibitors of 14 kDa PLA2 are without an effect in this assay (assay E). Alternatively, CoA-IT inhibitors will inhibit both LTC4 and PGE2 release from activated monocytes while selective PLA$_2$ inhibitors inhibit LTC4 release but spare prostanoid formation or production (assay F).

Disease slates which could benefit from the inhibition of lipid mediator production include, but are not limited to, adult respiratory distress syndrome, asthma, arthritis, reperfusion injury, endotoxic shock, inflammatory bowel disease, allergic rhinitis and various inflammatory skin disorders. Each of these disorders is mediated in some part by lipid mediators of inflammation. Compounds which inhibit CoA-IT, by virtue of their ability to block the generation of lipid mediators of inflammation, are of value in the treatment of any of these conditions. Similarly compounds which inhibit PLA$_2$, by virtue of their ability to block the generation of lipid mediators of inflammation stemming from activation and/or release of this enzyme are of value in the treatment of these conditions. In particular, an inhibitor of CoAIT, for instance would offer an advantage over the classical NSAIDs which affect only prostanoid production (and not PAF biosynthesis) thereby inhibiting both the acute and cell-mediated "chronic" inflammatory processes. Further an advantage of the $PLA_2$ inhibitor would be theft affect on human monocyte leukotrienes and PAF formation, while immunosuppressive prostanoids, such as $PGE_2$, are spared.

Treatment of disease states caused by these lipid inflammatory mediators i.e., arachidonate, eicosanoids and PAF, include certain cardiovascular disorders such as but not limited to, myocardial infarction, stroke, circulatory shock, or hypotension, ischemia, reperfusion injury; inflammatory diseases such as, but not limited to, arthritis, inflammatory bowel disease, Crohn's disease, or ulceralive colitis; respiratory diseases such as but not limited to, asthma, or adult respiratory distress syndrome; analphylaxis, shock, such as but not limited to endotoxic shock; topical disesases, such as but not limited to actinic keratosis, psoriasis, or contact dermatitis; or pyresis.

In order to use a compound of formula (I)/(II) or a pharmaceutically acceptable salt thereof in therapy, it will normally be formulated into a pharmaceutical composition in accordance with standard pharmaceutical practice. This invention, therefore, also relates to a pharmaceutical composition comprising an effective, non-toxic amount of a compound of formula (I) and a pharmaceutically acceptable carrier or diluent.

Compounds of formula (I) or (II), pharmaceutically acceptable salts thereof and pharmaceutical compositions incorporating such may conveniently be administered by any of the routes conventionally used for drug administration, for instance, orally, topically, parenterally or by inhalation. The compounds of formula (I)/(II) may be administered in conventional dosage forms prepared by combining a compound of formula (I) or (II) with standard pharmaceutical carriers according to conventional procedures. Such pharmaceutically acceptable carriers or diluents and methods of making are well known to those of skill in the art, and reference can be found in such texts as Remington's Pharmaceutical Sciences, 18th Ed., Alfonso R. Genarao, Ed., 1990, Mack Publishing Co. and the Handbook of Pharmaceutical Excipents, APhA Publications, 1986.

The compounds of formula (I) or (II) may also be administered in conventional dosages in combination with known second therapeutically active compounds, such as steroids or NSAID's for instance. These procedures may involve mixing, granulating and compressing or dissolving the ingredients as appropriate to the desired preparation. It will be appreciated that the form and character of the pharmaceutically acceptable carrier or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid careers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an are pule or nonaqueous liquid suspension.

Compounds of formula (I)/(II) may be administered topically, that is by nonsystemic administration. This includes the application of a compound of formula (I)/(II) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as siliceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98°–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Each dosage unit for oral administration contains preferably from 1 to 500 mg (and for parenteral administration cones preferably from 0.1 mg to 100 mg) of a compound of the structure (I) or a pharmaceutically acceptable salt thereof calculated as the free base.

The pharmaceutically acceptable compounds of the invention will normally be administered to a subject in a dally dosage regimen. For an adult patient this may be, for example, an oral dose of between 1 mg and 500 mg, preferably between 1 mg and 250 mg, or an intravenous, subcutaneous, or intramuscular dose of between 0.1 mg and 100 mg, preferably between 0.1 mg and 25 mg, of the compound of the Formula (I)/(II) or a pharmaceutically acceptable salt thereof calculated as the free base, the compound being administered from 1 to 4 times per day.

The choice of form for administration, as well as effective dosages, will vary depending, inter alia, on the condition being treated. The choice of mode of administration and dosage is within the skill of the art.

BIOLOGICAL METHODS

To determine activity of the compounds of Formula (I) and (II) various cellular assays can be used to determine in vitro activity. Additionally, various classical in vivo acute inflammatory models which have some aspect of their etiology to elevated eicosanoid levels can be employed, such as the paw edema model, zymosan peritonitis, reverse Arthus pleurisy or various skin inflammation assays which are described in Lewis et al., Experimental Models of Inflammation, in the *Handbook of Inflammation*, Vol. 5, Bonta Ed., Elsevier Science Publishers, New York (1985) whose disclosure is herein incorporated by reference. The TPA induced ear edema model (mouse) as well as the carrageenan paw edema model in the rat arc described herein as well. These classical models of inflammation will reflect the drug's ability to alter an inflammatory response but cannot address the specificity of drug action. These models have been traditionally designed as non steroid antiinflammatory drug sensitive pharmacological screens and it is important to utilize models which can differentiate $PLA_2$ and CoA-IT inhibitors from NSAIDS.

Cell-free and Cellular Assessment of Inhibitors

Described herein are several in vitro assays both for CoA-IT and $PLA_2$ enzyme activities. The first employs purified recombinant enzyme or a broken cell assay, assay (a or b, respectively) described below. Alternatively, evaluation of inhibitors can occur in intact cells such as described in the assay, assay (c and d) below. CoA-IT activity can exclusively be measured, and differentiated from $PLA_2$ inhibition, in intact cells by following the movement of a pulse of [$^3$H] arachidonate as it moves into the 1-alkyl and 1-alkenyl phospholipids in inflammatory cells (assay e). It should be noted for the purposes herein that assays c, d, & f can both be used for $PLA_2$ and CoA-IT inhibition determination.

Inflammatory Responses in vivo

The ability of compounds that inhibit CoA-IT and/or $PLA_2$ to affect in vivo inflammatory responses may be assessed. Inflammatory responses are induced in the mouse ear by the topical application of a pro-inflammatory agent, such as 12-O-tetradecanoylphorbol 13-acetate (assay g). This produces an edematous response, as measured by increases in ear thickness, as well as increased inflammatory cellular infiltrate, as measured by increases in myeloperoxidase activity (as described in the methods). To further validate the mechanism of action inflammation induced by the direct adminstration of arachidonic acid can be used. In this case compounds altering arachidonic acid mobilization or liberation should be with our effect.

In Vitro Assays

Assay (a): Phospholipase $A_2$ assay:

Phospholipase $A_2$ activity of rh Type II-14 kDa $PLA_2$ or $PLA_2$ semi-purified from human synovial joint fluid was measured by the acylhydrolysis of high specific activity (NEN)[$^3$H]-AA-*E. coli* (0.5 mCi/5nmol PL Pi) as previously described in Marshall et at., J. Rheumatology, 18:1, pp59–65 (1991). High specific activity [3H]AA-*E. coli* had up to 95% of the label incorporated into phospholipid which was localized almost exclusively in the sn-2 position, as demonstrated by purified 14kDa PLA2 or low molecular weight $PLA_2$ acylhydrolysis and separation of products by thin layer chromatography CILC) (data not shown). [Predominately used herein was rh Type II 14 kDa PLA2, or alternatively bovine pancreatic $PLA_2$ was also be used]. The reaction mixture (50 or 100 ml total volume) contained 25 mM HEPES, pH 7.4, 150 mM NaCl, 5 mM $CaCl_2$ and [$^3$H]-AA-*E. coli* (low specific activity; 5–8 nmol PL Pi per assay). Assays were incelbated for a time predetermined to be on the linear portion of a time versus hydrolysis plot. Experiments were conducted with final % hydrolysis values ranging from 2% (400–1000 dpm) to 10% (2000–5000 dpm) acylhydrolysis after blank correction. Reactions were terminated by the addition of 1.0 mL tetrahydrofuran (THF). The whole sample was placed over aminopropyl solid phase silica columns and eluted with THF:acetic acid (49:1) exclusively separating free fatty acids with greater than 95% recovery. Radiolabel in this eluate was quantitated by liquid scintillation counting. Results were expressed as % of fatty acid hydrolyzed ([sample dpms–non-specific (blank) dpms/total dpms]×100) or specific activity which was calculated from hydrolysis values found in the linear portion of time versus % hydrolysis plots (pmol free fatty acid hydrolyzed mg/min). Non-specific activity was always less than 1% of the total counts added.

Protein determination

All protein concentrations were determined by Bradford protein analysis kits (Biorad, Richmond, Calif.).

Results:

Representative compounds of Formula (I), Examples 1 and 2, demonstrated positive $PLA_2$ inhibition, generally tested at 50 μm levels.

Assay (b): CoA-IT Activity

The following is a method to measure CoA-IT activity and the effects of compounds on CoA-IT activity. The assay is based upon mixing cellular material containing CoA-IT activity with a stable lyso phospholipid such as 1-alkyl-2-acyl-GPC and measuring the production of phospholipid product such as 1-alkyl-2-acyl-GPC occurring in the absence of added CoA or CoA-fatty acids.

Cell Preparation

Any inflammatory cell that contains high levels of CoA-IT activity can be used, such as neutrophils, macrophages or cell lines such as U937 cells. U937 cells were obtained from American Type Culture Collection and grown in RPMI-1640 media (Gibco, Grand Island, N.Y.) supplemented with 10% fetal bovine serum (Hyclone, Logan, Utah) at 37° C., 5% $CO_2$. Cells were grown without differentiation (basal state) by any agent, such as dimethyl sulfoxide. As used herein, "inflammatory cells" include, but are not limited to neutrophils, macrophages, monocytes, lymphocytes, eosinophils, basophils, and mast cells.

Microsomal preparation

Microsomes are prepared using standard techniques. In this case, cells are washed with a buffer of 250 mM sucrose, 10 mM Tris, 1 mM EGTA, 1 mM $MgCl_2$, pH 7.4 and ruptured by $N_2$ cavitation (750 psi, 10 minutes). The ruptured cells are centrifuged 1000×g, 5 minutes. The resulting supernatant is centrifuged at 20,000×g,~20 minutes. Microsomes are prepared from this supernatant by centrifugation at 100,000×g, 60 minutes. The resulting pellet is washed once with assay buffer (150 mM NaCl, 10 mM $Na_2KPO_4$, 1 mM EGTA, pH 7.4), recentrifuged and the pellet resuspended in assay buffer (4–20 mg protein/ml) and is stored at −80° C. until assayed.

CoA-IT activity

CoA-IT activity is measured in 1.5 ml centrifuge tubes in a total volume of 100 ul. Microsomes are diluted in assay buffer to the desired protein concentration (6–20 ug/tube). The reaction is initiated by addition of [3H]1-alkyl-2-lyso-sn-glycero-3-phosphocholine (GPC) (~0.1 uCi/tube) and 1 µM final cold 1-alkyl-2-lyso-GPC in assay buffer with 0.25 mg/ml fatty acid-poor bovine serumalbumin (BSA) (Calbiochem, La Jolla, Calif.). [3H]1-alkyl-2-lyso-GPC, approximately 50 Ci/mmol, is from NEN-Dupont (Boston, Mass.) and cold 1-alkyl-2-lyso-GPC is from Biomol (Plymouth Meeting, Pa). Microsomes are pretreated with desired agents for the desired time (10 minutes) before the addition of [3H]1-alkyl-2-lyso-GPC. The reaction is run for the desired time (10 minutes) at 37° C. The reaction is stopped and the lipids extracted by addition of 100 ul of chloroform:methanol (1:2, v/v) followed by 100 ul of chloroform and 100 ul of 1M KCl. The samples are vortexed and centrifuged at high speed in a microfuge for 2–3 minutes. An aliquot of the chloroform-extracted materials are separated, usually by TLC in chloroform/methanol/acetic acid/water (50:25:8:4, v/v), visualized by radioscanning (Bioscan) and the product, [3H]1-alkyl-2-acyl-GPC, is scraped and quantified by liquid scintillation spectroscopy. With this TLC system, the synthetic standards of 1-alkyl-2-lyso-GPC and 1-alkyl-2-acyl-GPC are well separated, with Rf values of approximately 0.25 and 0.65, respectively. Other methods can be used to separate substrate from product, including but not limited to column chromatography, affinity chromatography and post reaction derivitization.

Protein concentration are assessed using the protein assay reagents from Bio-Rad (Richmond, Calif.).

Results

A variety of compounds have been tested in this assay to determine its selectivity and inability to detect trivial, non-selective inhibitors. Inhibitors of 5-1-lipoxygenase (5-LO) and cyclooxygenase (CO), such as indomethicin, naproxen, 6-(4'-Fluorophenyl)-5-(4-pyridyl)-2,3-dihydroimidzo-[2,1-b]thiazole and 6-(4'-Fluorophenyl)-5-(4-pyridyl)2,3-dihydroimidzo-[2,1-b]thiazole-dioxide had no effect on CoA-IT activity at concentrations up to 100 µM. The anti-oxidant BHT also has no effect at concentrations up to 100 µM. Compounds which complex with phospholipids and inhibit $PLA_2$ activity, such as quinacrine and aristolochic acid have no effect on CoA-IT activity at concentrations up to 500 µM. Doxepine, a compound reported to inhibit PAF release did not inhibit CoA-IT at concentrations up to 100 µM. Sodium diclofenac, reported to decrease leukotriene production by altering arachidonic acid metabolism, had no effect on CoA-IT activity at concentrations up to 500 µM. These results show that the assay for CoA-1T activity is sensitive and selective.

Results:

A representative compound of Formula (I), Example 1, N-[3-(7-phenylheptylamido)-4-(4-phenylmethyl)phenylthio]-butyl-N-hydroxy urea demonstrated positive CoA-IT inhibitory activity, generally tested at 50 µm levels. The compound of Example 2, did not demonstrate positive activity in this assay at levels of greater than 30 uM.

Assay (c): Arachidonic Acid Release Assay

Preparation of human neutrophils

Human neutrophils are obtained in the laboratory using three different methods. One method uses leukophoresis packs from normal humans and neutrophils are isolated using the histopaque-1077 technique. The blood is centrifuged at 300×g for 10 minutes. The cell pellets are resuspended in PBS composed of 137 mM NaCl, 8.8 mM Na2HPO4, 1.5 mM KH2PO4, 2.7 mM KCl (Dulbecco's Gibco Laboratories, Long Island, N.Y.) and layered over histopaque-1077 (Sigma, St. Louis, Mo.). The pellets are collected after centrifugation (300×g for 30 minutes) and washed once in PBS. The cell pellets are exposed briefly to deionized water to lyse any erythrocytes. The remaining cells are collected by centrifugation, suspended in PBS, counted and identified after cytospinning and staining. The final leukocyte preparation will be of greater than 95% purity and viability.

The second method isolates human neutrophils from fresh heparinized normal blood using the Histopaque-1077 technique. The blood is layered over Histopaque-1077 (Sigma, St. Louis, Mo.) and centrifuged at 400×g for 30 minutes. The cell pellets are resuspended in 35 ml of PBS and 12 ml of 6% Dextran, followed by Dextran sedimentation at room temperature for 45 minutes. The upper layer is collected and further centrifugated for 10 minutes at 1000 rpm. The cell pellets are exposed briefly to deionized water to lyse erythrocytes. The remaining cells are collected by centrifugation, suspended in PBS, counted and identified after cytospinning and staining. The final leukocyte preparation will be of greater than 95% purity and viability.

The third method isolates human neutrophils from freshly drawn heparinized normal blood using the Percoil technique. The blood is first treated with 6% Dextran at room temperature for a 1 hour sedmination. The upper layers of plasma are collected and centrifuged at 400×g for 10 minutes. The cell pellets are resuspended in Percoll 1.070 g/ml supplemented with 5% fetal bovine serum and layered on discontinuous gradients (1.080, 1.085, 1.090, 1.095 g/ml) followed by centrifugation at 400×g for 45 minutes. The neutrophils are collected from interfaces of 1.080 and 1.085 and the 1.085 and 1.090 Percoil densities, followed by a centrifugation at 400×g for 45 minutes. The neutrophils are suspended in PBS, counted and identified after cytospinning and staining. The final leukocyte preparation will be of greater than 95% purity and viability.

There should be no difference noted in the response of the neutrophils nor in the effects of test compounds in neutrophils isolated by the three different techniques.

Treatment of human neutrophils

Neutrophils are suspended in PBS with 1 mM $Ca^{2+}$ and 1.1 mM $Mg^{2+}$ at concentrations of 5 to 20×106 cells per ml. Cells are added to test tubes and treated with the desired compounds for 5 to 10 minutes, then challenged with calcium ionophere A23187, 2 µM, or vehicle control, PBS containing 0.25–1 mg/ml BSA. After 5 to 20 minutes, the reactions are terminated by addition of an equal volume of chloroform:methanol (1:2, v/v) to the samples. [$^2H_8$]Arachidonic acid (50, 100 or 200 ng) is added as an internal standard and the lipids ware extracted by addition of equal volumes of chloroform and distilled water. The samples are vortexed and centrifuged at high speed and the chloroform layer removed to a clean tube.

Quantitation of Stimulated-PMN AA Liberation by Gas Liquid Chromatography Neutrophil suspensions ($3\times10^7$ cells/3 ml) in Hanks balanced salt solution with $Ca^{2+}$ and $Mg^{2+}$ were pre-incubated with compound for 10 min prior to addition of A23187 (2 µM) for 10 min. The reaction was terminated by extraction lipids by the method of Bligh and Dyer (Can. J. Biochem. Physiol. (1959) 37, 911–917) and the fatty acid 22:3 [13,16,19-Docosatrienoic acid] (0.5 ug) was added as an internal standard. The organic phase was removed and samples were double extraced. The organic layers were comvined then dried under a stream of argon. The lipiris were resuspended in 2 ml hexane and free fatty ackds seperated from the other lipids using a modification of the silic acid column method described by Winkler et at., BioChem. J., 291:825–831 (1993), whose disclosure is incorporated herein by reference. Each sample in hexane was passed over a 500 mg silica solid phase column (pre-conditioned with 2 ml hexane). This was followed by 4 ml of chloroform. An exclusive fatty acid enriched fraction was then eluted with 2 ml hexane:ethyl ether (1:1 v/v) Recovery of free fatty acids was 95–98% as assessed using radiolabled AA or cold AA. The fatty acid fraction was dried under a stream of argon and fatty acids wsere converted to methyl esters by adding 1 volume of 4% surfuric acid in methanoland heating the solution for 1 hr at 60° C. as previously described in Marshal et at., J. Pharm. Exper. Therap., 268: 1–9 (1994) whose disclosure is incorporated herein by reference. Fatty acid methyl esters were extracted by the addition of 1 volume of hexane and 1 volume of water. The hexane layer was removed and stored at −20° C. until analyzed by gas liquid. chromatography (GLC). Samples were reduced in volume to 5 ul by evaporation under argon and injected onto a fused silica column (30 m×0.32 mm; Supelco, Bellfont, Pa.) over 48 min using a temperature gradient (140°–196° C.). Peaks were identified by comparison of retention times obtained by running known standards (Nuchek Prep, Elysian, Minn.). The quantity of each fatty acid was calculated from its peak area signal intensity compared with that of the internal standard, 22:3n-9, and calculated as ng free fatty acid/cell concentration.

Results:

Representative compounds of Formula (I), Examples 1 and 2, demonstrated weak inhibitory activity in this assay, at levels greater than 10 uM.

Assay (d): Assay for Production of Platelet-Activating Factor (PAF)

Preparation of human neutrophils:

Blood is obtained from normal humans and neutrophils are isolated as described for the arachidonic acid release assay, above. The final leukocyte preparation should be of greater than 95% purity and viability.

Treatment of human neutrophils

Neutrophils are suspended in PBS at concentrations of 5 to $20\times10^6$ cells per ml. Cells are added to test tubes and treated with the desired compounds for 5 to 10 minutes, then challenged with calcium ionophore A23187, 2 µM and 20–30 µCi of [3H]acetic acid (NEN-Dupont, Boston, Mass.), or the vehicle of PBS with 0.25–1 mg/ml. After 5 to 20 minutes, the reactions are terminated by addition of an equal volume of chloroform:methanol (1:2, v/v) to the samples and the lipiris are extracted by addition of equal volumes of chloroform and distilled water. The samples are vortexed and centrffuged at high speed and the chloroform layer removed to a clean tube.

Assay for PAF

The chloroform from each tube is evaporated to dryness and the material suspended in a small volume of chloroform or chloroform:methanol (25–100 µl) and the total material spotted on a Silica TLC plate. The plates are developed in chloroform/methanol/acetic acid/water (50:25:8:4, v/v) visualized by radioscanning (Bioscan) and the product, [$^3$H]PAF, is scraped and quantified by liquid scintillation spectroscopy. With this TLC system, the Rf value for a synthetic standard of PAF is approximately 0.33.

Results:

A representative compound of Formula (I), Example 1, N-[3-(7-phenylheptylamido)-4-(4 -phenylmethyl)phenylthio]-butyl-N-hydroxy urea demonstrated positive inhibitory activity in this assay, showing an IC50 of about 10 uM. The compound of Example 2 did not demonstrate positivr activity in this assay at greater than 30 uM.

Assay (e): Methods for the evaluation of CoA-IT inhibitors on mobilization of labeled arachidonic acid in intact cells Measurement of the effect of CoA-IT inhibitors on the transfer of [$^3$H]arachidonate into 1-ether phospholipids in non-stimulated inflammatory cells can be accomplished by general application of the following specific method. Human neutrophils are isolated and resuspended ($5\times10^7$/ml) in Hanks Balanced Salt Solution (HBSS; Gibco). [5,6,8,9,11,12,14,15-$^3$H]-Arachidonic acid (100 Ci/mmol; New England Nuclear) complexed to 200 µl HBSS containing 0.25 mg/ml HSA is added to the cell suspension (1 µCi/ml). The cells are incubated with gentle shaking at 37° C. for 5 min. The reaction is terminated by the addition of 40 ml ice-cold HBSS containing HSA (0.25 mg/ml). The cells are then removed from the supernatant fluid by centrifugation (225 g, 8 min). Unincorporated [$^3$H]-arachidonic acid is completely removed by two more washes of HBSS containing 0.25 mg/ml HSA. The neutrophils are resuspended in fresh buffer, exposed to various concentrations of a CoA-IT inhibitor or its vehicle and incubated without stimulation for 2 hrs. At that time, the tubes containing the cells and buffer are extracted (Bligh & Dyer [Can. J. Biochem. Physiol. (1959) 37, 911–917]) and the phospholipid classes are separated and collected by normal phase HPLC, using a Ultrasphere Silica column (4.6 mm×250 mm; Rainin) eluted with hexane/2-propanol/ethanol/phosphate buffer (pH 7.4)/acetic acid (490:367:100:30:0.6 v/v) for 5 min at a flow rate of 1 ml/min. The amount of phosphate buffer in the eluting solvent is increased to 5% over 10 min and this solvent composition is maintained until all the phospholipid classes is eluted from the column (30–40 min) (Chilton, F. H. [Methods Enzymol. (1990) 187, 157–166]). The phospholipids are converted into diradylglycerols by addition of phospholipase C, 20 units–40 units of Bacillus cereus phospholipase C (Sigma Type XIII) in 100 mM Tris HCl buffer (pH 7.4) for 2.5–6 hr, then converted into 1,2-diradyl-3-acetylglycerols by incubation with acetic anhydride and pyridine (Chilton, F. H. [Methods Enzymol. (1990) 187, 157–166]). The phospholipid subclasses are separated by TLC in benzene/hexane/ethyl ether (50:45:4, v/v), located by image analysis (Bioscan) and the amount of radioactivity in each class is determined by zonal scraping and liquid scintillation counting.

The following is the method for assessing the ability of a compound to alter arachidonate content of cellular phospholipids, which can be generalized for any desired cell. Specifically, mouse bone marrow-derived mast cells are removed from culture and provided with exogenous [$^3$H] arachidonic acid for 30 minutes. The labeled arachidonic acid which had not been incorporated into the cells is then removed by washing the cells 2 times with an albumin-containing buffer. At that point, the cells are treated with various concentrations of CoA-IT inhibitors and then placed back in culture for 24–48 hours. The phospholipids are extracted by the method of Bligh and Dyer [Can. J. Biochem. Physiol. (1959) 37, 911–917] and phospholipids separated by normal phase HPLC by the method of Chilton [Methods Enzymol. (1990) 187, 157–166]. The radioactive and mole quantities of arachidonate in complex lipids are determined. At this point, cellular lipid extracts are treated with KOH (0.5M) to remove fatty acids from complex lipids (phospholipids) and the quantities of arachidonate in these extracts can then be determined by various methods, including gas chromatography and mass spectrometry (Chilton [Methods Enzymol. (1990) 187, 157–166]).

Assay (f): Measurement of stimulated eicosanoid release by human monocytes.

Human Monocyte Isolation.

Leukocyte-rich leukopaks obtained from Biological Specialties (Lansdale, Pa.) are collected from male volunteers who are not taking anti-inflammatory drugs. Leukopaks are centrifuged (90×g for 15 min) twice to remove the platelet-rich plasma. The cell pellet is washed by centrifugation and are resuspended in HBSS without $Ca^{2+}$ or $Mg^{2+}$. Histopaque 1077 is layered under the cell suspension and centrifuged at 400×g for 30 min to obtain the buffy coat. The interfacial buffy coat, containing monocytes and lymphocytes, is removed and saved. The buffy coat is washed twice with HBSS without $Ca^{2+}$ or $Mg^{2+}$ by centrifugation. The cell pellet (4–6×$10^8$ cells/30 mls) is resuspended in iso-osmotic media (RPMI-1640, 10% heat inactivated fetal bovine serum (FBS), 0.2 mM L-glutamine, 2.5 mM HEPES) and layered over an equal volume of 46% Percol mixture (10× PBS/Percol; 9.25/0.75) and 54% iso-osmotic media and centrifuged for 30 min at 1000×g (Marshall and Roshak, Biochem. Cell Biol. 71: 331–339, 1993). The monocyte population located at the interface of the Percoll gradient is removed and washed twice in HBSS without $Ca^{2+}$ or $Mg^{2+}$. This resulted in a greater than 85–90% pure monocyte population as assessed by differential staining.

Measurement of Stimuli-Induced Eicosanoid Release.

Monocytes (5×$10^6$/ml are incubated as a suspension in serum-free RPMI-1640 medium containing the vehicle DMSO (<1%) or drug for 30 min at 27° C. after which vehicle or stimuli is added for the indicated time. The stimulating agent is solubilized in DMSO and appropriate vehicle controls are included in all experiments. The amount of stimuli is chosen from the linear portion of a concentration versus product curve usually representing 60–80% maximal stimulation over the indicated incubation time at 37° C. (A23187, 1 µM, (15 min). The reaction is terminated by reduction of pH through addition of citric acid and centrifugation (10 min, 400×g, 4° C.). Cell viability is monitored before and after experiments using trypan blue exclusion. The cell-free media is decanted and stored at –70° C. until analyzed. Prostaglandin $E_2$ and $LTC_4$ are directly measured in cell-free media using enzyme immunoassay (EIA) kits purchased from Caymen Chemical Co. (Ann Arbor, Mich.) Sample or standard dilutions are made with appropriate media and analyzed in triplicate. Results are obtained by extrapolation from a standard curve prepared in the media and expressed as pg or ng/ml of sample.

Representative compounds of Formula (I) herein which demonstrated positive activity in this assay, with human monocyte cells, is (±) N-[3-(7-phenylheptylamido)-4-(4-phenylmethyl)phenylthio]-butyl-N-hydroxy urea which had an $IC_{50}$ of $PGE_2$ less than 0.1 µM and for $LTC_4$ and $IC_{50}$ of 0.22 µM; the compound [3-(7-Phenylheptylamido)-4-(4-phenylmethyl)phenylthio]-butylnitrile demonstrated an $IC_{50}$ for $PGE_2$ of about 0.1 µM and for $LTC_4$ and $IC_{50}$ of 0.521 µM.

In vivo assays

Assays (g and h): Assay (Method) for TPA (assay g) or Arachidonic acid (assay h)-induced Inflammation Animals:

Male Balb/c inbred mice are obtained from Charle River Breeding Laboratories (Kingston, N.Y.). Within a single experiment mice (22–25 g) are age-matched. These in vivo experiments typically involve the use of 5–6 animals/group.

(g) TPA-induced Mouse Ear Inflammation:

Assay of Ear Edema

TPA (12-0-tetradecanoylphorbol 13-acetate) (Sigma Chemical Company) in acetone (4 mg/20 ml) is applied to the inner and outer surfaces of the left ear of BALB/c male mice. The thickness of both ears is then measured with a dial micrometer (Mitutoyo, Japan) at both 2 and 4 hours after treatment, and the data expressed as the change in thickness ($10^{-3}$ cm) between treated and untreated ears. The application of acetone does not cause an edematous response; therefore, the difference in ear thickness representes the response to the TPA. After measuring the edema, the inflamed left ears are removed and stored at –70° C. until they were assayed for MPO (myeloperoxidase) activity where appropriate.

Assay of Myeloperoxidase (MPO) in Inflamed Ear Tissue:

On the day of the assay, partially thawed ear tissues are minced and then homogenized (10% w/v) with a Tissumizer homogenizer (Tekmar Co.) in 50 mM phosphate buffer (pH 6) containing 0.5% HTAB. The tissue homogenates are taken through three cycles of freeze-thaw, followed by brief sonication (10 sec). The method of Bradley et at. is used with modifications as described. The appearance of a colored product from the MPO-dependent reaction of o-dianisidine (0.167 mg/ml; Sigma) and hydrogen peroxide (0.0005%; Sigma) is measured spectrophotometrically at 460 nm. Supernatant MPO activity is quantified kinetically (change in absorbance measured over 3 min, sampled at 15-sec intervals) using a Beckman DU-7 spectrophotometer and a Kinetics Analysis package (Beckman Instruments, Inc.). One unit of MPO activity is defined as that degrading one micromole of peroxide per minute at 25° C.

Statistics:

Statistical analysis is done using Student's "t" test. The $ED_{50}$ are values which cause a 50% inhibition of the inflammatory response and are calculated by regression analysis of the dose response data.

(h) Arachidonic acid induced ear inflammation assay

Arachidonic acid is dissolved in acetone (1 mg/ear) to the left ear of BALB/c male mice. The thickness of both ears is measured with a constant pressure thickness guage 1 hour after treatment and the data expressed as the change in thickness between treated and untreated ears. Test compounds or vehicle are given at the time of AA application. The inflammatory cell infiltration is measured by MPO activity as described above in the TPA ear edema assay. After the edema measurements are made, the inflamed ears are removed and assayed for MPO activity.

The anti-inflammatory effect of various standard inhibitors topically administered in the AA and TPA induced mouse ear edema model were measured for dexamethasone, scalaradial and Wyeth's compound WY 50,295 at does of 0.2, 0.1 and 0.3 respectively. The TPA % change in edema was −50(p<0.001), −46(p<0.01) and −18(ns) respectively; for AA the change was −10(ns), −11(ns) and −50(p<0.001). The change in MPO for TPA model was −54(p<0.001), −65(p<0.001) and −36(p<0.05) respectively; for AA it was 0(ns), −33(ns) and −90(p<0.001). One hypothesis is that the AA administration to the ear overrides the need for $PLA_2$ mediated liberation of substrate for subsequent proinflammatory lipid mediator generation or AA mobilization by CoA-IT. In this case an inhibitor of an AA-metabolizing enzyme should be effective while and inhibitor of $PLA_2$ would be ineffective. As noted above, scalaradial and dexamethasone have little or no effect in the AA ear model at concentrations which were effective in the TPA ear model. This can be contrasted to the activity of the selective 5-LO inhibitor WY 50,295 which strongly inhibits inflammation in response to AA. The AA ear model therefore responds well to compounds that exhibit 5-LO inhibitory action and appears to be uneffected by putative $PLA_2$ inhibitors. This model therefore provides a unique tool with which the contribution of the 5-LO inhibition to the in vivo anti-inflammatory activity of various compounds can be separated from LMW-$PLA_2$ inhibition.

Representative compounds of Formulas (I) and (II) demonstrated the following activity in these animal models.

Specifically in the TPA ear model, typically dosed at 50 mg/ear, the compound of Example 1 demonstrated activity as an inhibitor of the inflammatory cell infiltration. In edema, for instance, topically [for ear swelling, the percent change @ mg/ear] showed −43 @ 1 mg/ear and for the MPO activity, −68 @1 mg/ear.

In addition, for the AA ear model the compound of Example 1 demonstrated activity reduction in ear swelling of −36 @1 mg/ear and for MPO a demonstration of −53 @1 mg/ear.

Thus this demonstrates a clear utility in the treatment of topically administered diseases associated with inflammation as noted herein such as, but not limited to, inflammatory bowel disease, contact dermatoses, actinic keratosis, psoriasis, or conjuctivitis.

As used herein, various abbreviations and explanations are as follows: [$^3$H], a molecule that contains tritium atoms, a radioactive isotope; A23 187, a compound that allows free entry of calcium into a cell; AA, arachidonic acid; arachidonate, arachidonic acid contained within a phospholipid; free arachidonic acid, arachidonic acid that is not contained within a phospholipid; [$^2H_8$]arachidonic acid, the form of arachidonic acid labeled with 8 deuterium atoms, a stable isotope; 1-alkyl, 1-O-alkyl; 1-alkenyl, 1-O-alk-1'-enyl; BSA, bovine serum albumin; CoA, coenzyme A; CoA-IT, CoA-independent transacylase; DTT, dithiothreitol; EGTA, [ethylenebis(oxyethylenenitrilo)]tetra acetic acid, a calcium chelator; GPC, sn-glycero-3-phosphocholine; EDTA, a metal ion chelator; GPE, sn-glycero-3-phosphoethanolamine; GC/MS, gas chromatography and mass spectrometry; 5HETE, 5(S)-hydroxyeicosa-6,8,11,14-tetraenoic acid; 15HETE, 15(S)-hydroxyeicosa-5,8,11,13-tetraenoic acid; HL-60, American Type Tissue Culture designated cell line similar to a monocyte; $LTB_4$, leukotriene $B_4$; $LTC_4$, leukotriene $C_4$; $LTD_4$, leukotriene $D_4$; lyso PAF, 1-alkyl-2-lyso-GPC, lyso platelet-activating factor; $PLA_2$, phospholipase $A_2$; PBS, phosphate buffered saline; PAF, platelet activating factor, 1-alkyl-2-acetyl-GPC; PL, phospholipid; PC, phosphatidylcholine; PE, phosphatidylethanolamine, PI, phosphatidylinositol; PMN, polymorphonuclear neutrophilic cell, neutrophil; PS phosphatidylserine; Rf, the distance a compound travels as a fraction of the solvent front; TLC, thin layer chromatography; U937, American Type Tissue Culture designated cell line similar to a monocyte.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore, the Examples herein are to be construed as merely illustrative and not a limitation of the scope of the present invention in any way. The embodiments of the invention in which an exclusive property or privilege is claimed are defined as follows.

What is claimed is:

1. A compound of the formula:

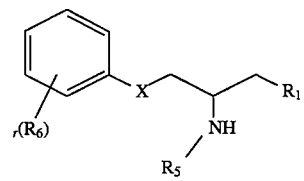

(I)

wherein $R_1$ is cyano;

$R_5$ is $C(O)(CH_2)_q$aryl or $S(O)_2(CH_2)_q$aryl;

q is an integer having a value of 1 to 18;

X is carbon, oxygen, —$NC_{1-4}$ alkyl, or sulfur;

$R_8$ is independently hydrogen or alkyl$_{1-6}$;

$R_6$ is independently selected from hydrogen, halogen, alkyl$_{1-5}$, cycloalkyl$_{5,8}$, hydroxy, (CHY)$_r$carboxy, alkoxy$_{1-5}$, thioalkyl$_{1-5}$, sulphinylalkyl$_{1-5}$, sulphonylalkyl$_{1-5}$, halosubstituted alkyl$_{1-6}$, (CHY)$_r$N($R_8$)$_2$, cyano or an optionally substituted aryl $C_{1-4}$alkyl;

r is an integer having a value of 1 or 3;

t is a number having a value of 0 or 1;

Y is hydrogen or alkyl$_{1-4}$;

or pharmaceutically acceptable salt thereof.

2. The compound according to claim 1 wherein $R_6$ is an optionally substituted aryl$C_{1-4}$alkyl.

3. The compound according to claim 1 wherein X is oxygen.

4. The compound according to claim 1 wherein $R_5$ is $C(O)(CH_2)_q$aryl; aryl is an optionally substituted phenyl.

5. The compound according to claim 4 wherein q is an integer of 5 to 7.

6. The compound according to claim 1 which is [(±)-3-(7-Phenylheptylamido)-4-(4-phenylmethyl)phenylthio]butylnitrile.

7. A pharmaceutical composition comprising a compound according to claim 1 and a pharmaceutically acceptable carrier or diluent.

8. A method for treating an inflammatory disease or disorder in a mammal in need thereof which method comprises administering to said mammal an effective amount of a compound according to claim 1.

9. The method according to claim 8 wherein the inflammatory disease or disorder is allergic rhinitis, ischemia, reperfusion injury, arthritis, inflammatory bowel disease, Crohn's disease, ulcerative colitis, asthma, adult respiratory distress syndrome, analphylaxis, actinic keratosis, psoriasis, contact dermatitis, or pyresis.

10. The method according to claim 9 wherein the inflammatory disease or disorder is mediated by lipid inflammatory mediators, arachidonic acid, its metabolites and/or platelet activating factor (PAF).

11. The method according to claim 10 wherein the lipid inflammatory mediators are inhibited by the an inhibitor of the enzyme phospholipase $A_2$($PLA_2$).

* * * * *